US00PP19908P2

(12) United States Plant Patent
Hilder et al.

(10) Patent No.: US PP19,908 P2
(45) Date of Patent: Apr. 14, 2009

(54) ***ALLAMANDA* PLANT NAMED 'SIAM SNOW'**

(50) Latin Name: *Allamanda carthartica*
Varietal Denomination: Siam Snow

(76) Inventors: Ronald Richard Hilder, 83 Allens Road, Upper Stone via Ingham, Queensland (AU), 4850; Gloria Ellen May Hilder, 83 Allens Road, Upper Stone via Ingham, Queensland (AU), 4850

( * ) Notice: Subject to any disclaimer, the term of this patent is extended or adjusted under 35 U.S.C. 154(b) by 6 days.

(21) Appl. No.: 11/807,850

(22) Filed: May 30, 2007

(51) Int. Cl.
*A01H 5/00* (2006.01)

(52) U.S. Cl. ..... Plt./263.1
(58) Field of Classification Search ..... Plt./263.1
See application file for complete search history.

(56) References Cited

PUBLICATIONS

GTITM Upovrom Plant Variety Database 2007/06 Citation for 'Siam Snow'as per QZ PBR 20051872; Oct. 10, 2005.*

* cited by examiner

*Primary Examiner*—Kent L Bell

(57) ABSTRACT

A new cultivar of *Allamanda* plant named 'Siam Snow' that is characterized by flowering during low light conditions and creamy white flowers.

1 Drawing Sheet

Botanical classification: *Allamanda carthartica.*
Variety denomination: 'Siam Snow'.

BACKGROUND OF THE INVENTION

The present invention relates to a new and distinct cultivar of *Allamanda* plant botanically known as *Allamanda carthartica* and hereinafter referred to by the cultivar name 'Siam Snow'.

The cultivar 'Siam Snow' was discovered and selected in 2002 as a single plant in Upper Stone via Ingram, Queensland, Australia. 'Siam Snow' was discovered growing in an outdoor bed of unnamed *Allamanda* cultivars. The exact parents are unknown.

Asexual reproduction of the new cultivar 'Siam Snow' first occurred by terminal cuttings in 2003 in De Lier, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Allamanda* cultivar 'Siam Snow'. These traits in combination distinguish 'Siam Snow' as a new and distinct cultivar apart from other existing known varieties of *Allamanda.*

1. *Allamanda* 'Siam Snow' exhibits flowering during low light conditions.
2. *Allamanda* 'Siam Snow' exhibits creamy white colored flowers.

The closest comparison cultivars are plants of the *Allamanda* species. 'Siam Snow' is distinguishable from plants of the species by the following characteristics:

1. 'Siam Snow' has creamy white flowers.
2. 'Siam Snow' exhibits longer lasting flowers.
3. 'Siam Snow' flowers readily under low light conditions.

BRIEF DESCRIPTION OF THE DRAWING

The accompanying photograph illustrates the distinguishing traits of *Allamanda* 'Siam Snow'. The plant in the photograph shows an overall view of a 2 year old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Allamanda* cultivar named 'Siam Snow'. Data was collected in Boskoop, The Netherlands from 2 year old glass greenhouse grown plants in 15 cm. diameter containers. The time of year was Winter and the temperature range was 20–22 degrees Centigrade during the day and 20–22 degrees Centigrade at night. The light level was natural outdoor light. Color determinations are in accordance with The Royal Horticultural Society Colour Chart 2001 edition, except where general color terms of ordinary dictionary significance are used. The growing requirements are similar to the species. 'Siam Snow' has not been tested under all possible conditions and phenotypic differences may be observed with variations in environmental, climatic, and cultural conditions, however, without any variance in genotype.

Botanical classification: *Allamanda carthartica* 'Siam Snow'.
Use: Ornamental Annual.
Parentage: The exact parents of 'Siam Snow' are unknown.
Vigor: Moderate to high.
Growth habit: Irregular upright.
Plant shape: Broad upright.
Suitable container size: 15 cm. pots.
Height: 80.4 cm. in height.
Width: 67.6 cm. in width.

Low temperature tolerance: USDA Zone 10.
High temperature tolerance: 40° Centigrade.
Propagation: Terminal cuttings.
Time to initiate roots: 56 days to initiate roots at 24–25° Centigrade.
Time to produce a rooted cutting or liner: 84 days at 24–25° Centigrade.
Growth rate: Approximately 15 cm. per month in spring.
Root system: Moderately fibrous.
Stem:
*Branching habit.*—Moderately branched.
*Pinching.*—Required.
*Number of lateral branches.*—Average 11 branches.
*Lateral branch length.*—44.8 cm.
*Lateral branch diameter.*—4.0 mm.
*Internode length.*—10.0 cm.
*Stem shape.*—Rounded and moderately glossy.
*Stem aspect.*—Rounded.
*Stem strength.*—Moderately strong.
*Stem color.*—Young twigs, 144B to 144A; older bark 197C.
*Pubescence.*—Lateral branches covered densely with short bristly hairs, 0.75 mm in length, 157D.
Foliage:
*Texture.*—Only slightly glossy.
*Leaf arrangement.*—In whorls of 4.
*Compound or single.*—Single.
*Quantity of leaves.*—Average 20; 5 whorls.
*Leaf shape.*—Elliptic to obovate and ovate.
*Leaf apex.*—Apiculate.
*Leaf base.*—Obtuse.
*Leaf length.*—9.2 cm. in length.
*Leaf width.*—4.3 cm. in width.
*Pubescence.*—Main veins and secondary veins on under sides densely covered with 0.75 mm hairs, 157D; Upper side has short hairs, 0.2 mm in length, 157D.
*Leaf margin.*—Entire, undulate.
*Young leaf color* (*lower surface*).—145B.
*Young leaf color* (*upper surface*).—144A.
*Mature leaf color* (*lower surface*).—In between 138B and 146C.
*Mature leaf color* (*upper surface*).—137A.
*Vein color* (*under surface*).—145B.
*Vein color* (*upper surface*): 146A.
*Venation pattern.*—Pinnate.
*Leaf attachment.*—Petiolate.
*Petiole dimensions.*—2 mm. in length, and 3 mm. in width.
*Petiole color.*—145B.
Flower:
*Inflorescence arrangement.*—In terminal and axillary pairs.
*Flowering habit.*—Continuous.
*Quantity of flowers per inflorescence.*—Average 2.
*Flower type.*—Single.
*Quantity of flowers per lateral stem.*—Average 1.
*Quantity of flower buds per lateral stem.*—Average 5.
*Quantity of flowers and buds per plant.*—44.
*Natural flowering season.*—Summer.
*Fragrance.*—None.
*Rate of flower opening.*—Flowers do not open simultaneously.
*Flower bud length.*—3.9 mm. in length.
*Flower bud diameter.*—1.1 mm. in diameter.
*Flower bud shape.*—Oblong.
*Bud color.*—145D with a dark tip 151C to 151D.
*Rate of bud opening.*—4 days.
*Flower aspect.*—Upright to outward.
*Flower shape.*—Funnelform.
*Flower dimensions.*—6.8 cm. in diameter and 7.1 cm. in height.
*Flower longevity.*—A few days.
*Petal appearance.*—Upper (inner) side dull, under (outer) side moderately glossy.
*Petal texture.*—Slightly leathery and smooth.
*Number of petal.*—5.
*Fused or unfused.*—Only the lower 70% are fused.
*Petal base.*—Attenuate.
*Petal arrangement.*—Fused into a funnelform.
*Petal shape.*—Spathulate, upper 30% orbicular.
*Petal margin.*—Entire, lower 70% fused.
*Petal apex.*—Retuse.
*Petal length.*—9.1 cm. in length.
*Petal width.*—2.6 cm.
*Petal color when opening* (*upper side*).—Lower narrow part N144A; upper wide part 2D, free part 155A to 155B, tinged 4B.
*Petal color when opening* (*under side*).—Lower narrow part N144A; upper wide part 2D, free part 4D.
*Petal color fully opened* (*upper side*).—Lower narrow part N144A; upper wide part 2D, free part 155A to 155B, tinged 4D.
*Petal color fully opened* (*under side*).—Lower narrow part N144A; upper wide part 2D, free part 4D.
*Petal color fading.*—Not fading.
*Self-cleaning or persistent.*—Self-cleaning.
Sepals:
*Number of sepals.*—Average 5.
*Sepal aspect.*—Rotate, fused at the base.
*Sepal shape.*—Oblanceolate.
*Sepal margin.*—Entire.
*Sepal apex.*—Acute.
*Sepal base.*—Fused cuneate.
*Sepal surface.*—Glossy and pubescent, hairs 0.5 mm, colored 157D.
*Sepal dimensions.*—2.6 cm. in length and 7 mm. in width.
*Young sepal color* (*upper side*).—145B with margins 145A.
*Young sepal color* (*under side*).—145B with margins 145A.
*Mature sepal color* (*upper side*).—145B with margins 145A.
*Mature sepal color* (*under side*).—145B with margins 145A.
Calyx:
*Calyx shape.*—Rotate.
*Calyx dimensions.*—6.8 cm. in length and 7.1 cm. in diameter.
Pedicels:
*Pedicel length.*—Average 8 mm.
*Pedicel diameter.*—Average 2 mm.
*Pedicel angle.*—Average 30° from lateral branch.
*Pedicel strength.*—Moderately strong.
*Pedicel color.*—144A.
Reproduction organs:
*Stamen number: Average* 5.
*Anther shape.*—Narrow triangular.

*Anther size.*—Average 5 mm in length.
*Anther color.*—164C.
*Amount of pollen.*—Very low.
*Pollen color.*—197C.
*Pistil number.*—Average 1.
*Pistil length.*—Average 2.6 cm. in length.
*Stigma shape.*—Capitate.
*Stigma color.*—145C.
*Style length.*—2.3 cm.
*Style color.*—150D.
*Ovary color.*—145D.

Disease and pest resistance: Plants of the new cultivar have not been observed for disease and pest resistance.

What is claimed is:

1. A new and distinct variety of *Allamanda* plant named 'Siam Snow' as described and illustrated.

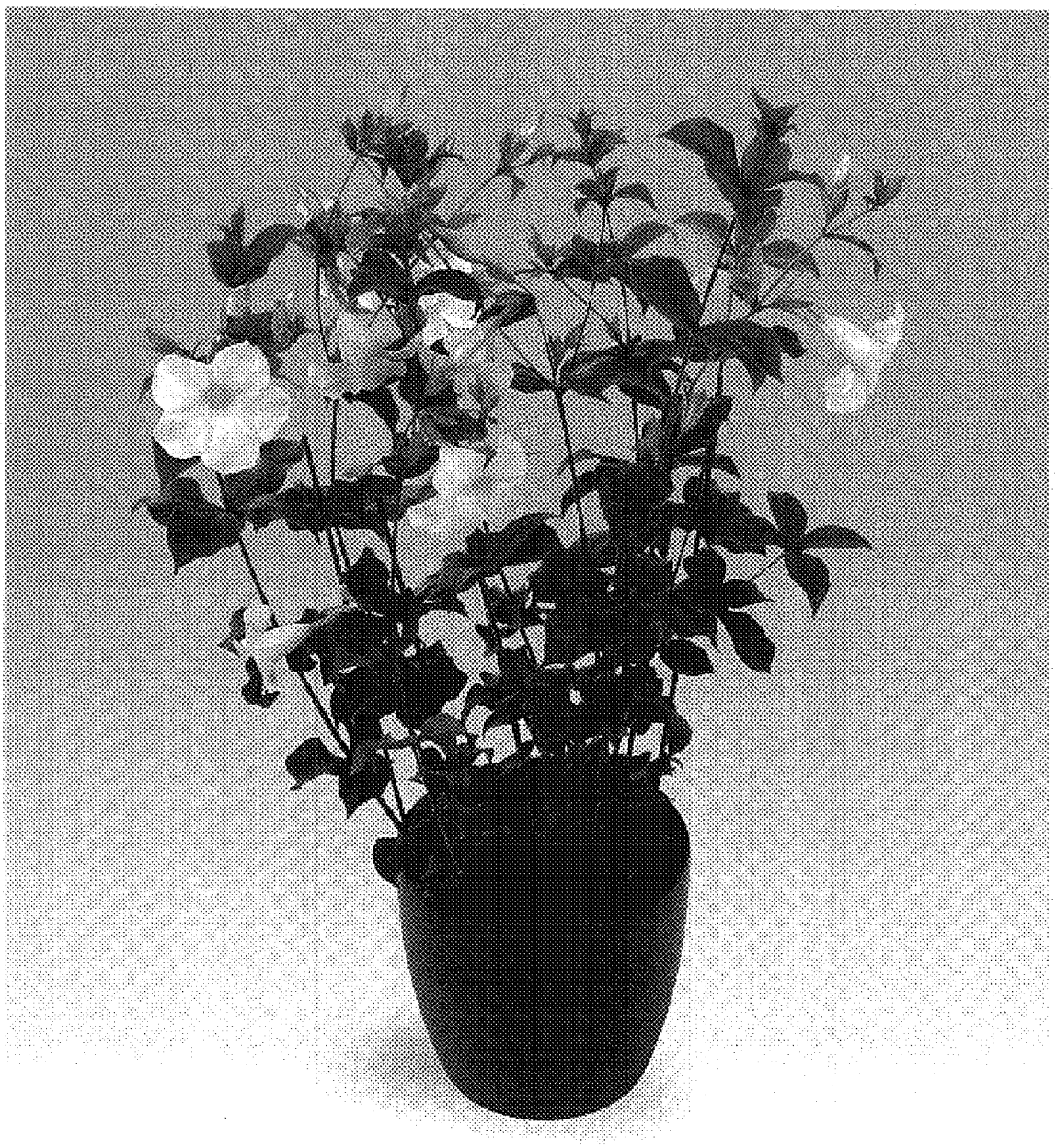

* * * * *